United States Patent [19]
Hickle et al.

[11] Patent Number: 6,056,953
[45] Date of Patent: May 2, 2000

[54] MATERIALS AND METHODS FOR THE CONTROL OF CALLIPHORIDAE PESTS

[75] Inventors: Leslie A. Hickle; Jewel Payne, both of San Diego, Calif.

[73] Assignee: Mycogen Corporation, San Diego, Calif.

[21] Appl. No.: 09/224,024

[22] Filed: Dec. 31, 1998

Related U.S. Application Data

[62] Division of application No. 08/856,226, May 14, 1997, Pat. No. 5,888,503, which is a division of application No. 08/249,780, May 26, 1994, abandoned, which is a division of application No. 08/093,199, Jul. 15, 1993, abandoned.

[51] Int. Cl.$^7$ ............................. A01N 63/02; C07K 14/32
[52] U.S. Cl. .................... 424/93.461; 424/405; 424/409; 435/252.3; 530/825
[58] Field of Search ............................. 424/93.461, 405, 424/409; 435/252.5; 530/825

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Hernstadt et al. | 424/84 |
| 4,849,217 | 7/1989 | Soares et al. | 424/93 |
| 4,853,331 | 8/1989 | Hernstadt et al. | 435/252.1 |
| 4,948,734 | 8/1990 | Edwards et al. | 435/252.5 |
| 5,151,363 | 9/1992 | Payne | 435/252.5 |

FOREIGN PATENT DOCUMENTS

| | | |
|---|---|---|
| 2786684 | 11/1984 | Australia . |
| 0409438 | 1/1991 | European Pat. Off. . |
| 0457498 | 11/1991 | European Pat. Off. . |
| 0480762 | 4/1992 | European Pat. Off. . |

OTHER PUBLICATIONS

Gaertner, F., L. Kim (1988) "Current Applied Recombinant DNA Projects" TIBTECH 6(4):S4–S7.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Gaertner, F. (1989) "Cellular delivery systems for insecticidal proteins: living and non–living microoganisms" Controlled Delivery of Crop–Protection Agents, pp. 245–255.

Krieg, V.A. et al. (1983) "*Bacillus thuringiensis* var. *tenebrionis*: ein neuer, gegenuber Larven von Coleopteran wirksamer Pathotyp" Z. ang. Ent. 96:500–508.

Hofte, H., H.R. Whiteley (1989) "Insecticidal Crystal Proteins of *Bacillus thuringiensis*" Microbiological Reviews 53(2):242–255.

Feitelson, J.S., J. Payne, L. Kim (1992) "*Bacillus thuringiensis*: Insects and Beyond" Bio/Technology 10:271–275.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Aronson, A.I. et al. (1986) "*Bacillus thuringiensis* and Related Insect Pathogens" Microbiological Reviews 50(1):1–24.

Pinnock, D.E. (1994) "The use of *Bacillus thuringiensis* for control of pests of livestock" Agriculture, Ecosystems and Environment 49:59–63.

Primary Examiner—Elizabeth C. Kemmerer
Assistant Examiner—David S. Romeo
Attorney, Agent, or Firm—Saliwanchik, Lloyd & Saliwanchik

[57] ABSTRACT

Methods and compositions for the control of pests of the family Calliphoridae are described. Specifically, *Bacillus thuringiensis* (*B.t.*) isolates having anti-calliphorid activity are disclosed. Also described are recombinant hosts which express *B.t.* genes coding for pesticidal toxins. The *B.t.* isolates and recombinant proteins are shown to be useful in a method for controlling calliphorids including screwworms and the sheep blowfly.

8 Claims, No Drawings

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

Met Ala Thr Ile Asn Glu Leu Tyr Pro Asn Val Pro Tyr Asn Val Leu
1               5                   10                  15

(2) INFORMATION FOR SEQ ID NO:2:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

Gln Leu Gln Ala Gln Pro Leu Ile Pro Tyr Asn Val Leu Ala
1               5                   10

(2) INFORMATION FOR SEQ ID NO:3:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:3:

Met Ile Ile Asp Ser Lys Thr Thr Leu Pro Arg His Ser Leu Ile Asn
1               5                   10                  15

Thr (2) INFORMATION FOR SEQ ID NO:4:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:4:

Ala Thr Leu Asn Glu Val Tyr Pro Val Asn
1               5                   10

(2) INFORMATION FOR SEQ ID NO:5:

(i) SEQUENCE CHARACTERISTICS:
       (A) LENGTH: 15 amino acids
       (B) TYPE: amino acid (C) STRANDEDNESS: single
        (D) TOPOLOGY: linear (ii) MOLECULE TYPE: protein (xi) SEQUENCE DESCRIPTION: SEQ ID NO:5:

Val Gln Arg Ile Leu Asp Glu Lys Leu Ser Phe Gln Leu Ile Lys
1               5                   10                  15

(2) INFORMATION FOR SEQ ID NO:6:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

GGACCAGGAT TTACAGGWGG RRA                                           23

(2) INFORMATION FOR SEQ ID NO:7:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

TAACGTGTAT WCGSTTTTAA TTTWGAYTC                                     29

(2) INFORMATION FOR SEQ ID NO:8:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

CAAYTACAAG CWCAACC                                                  17

(2) INFORMATION FOR SEQ ID NO:9:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

TTCATCTAAA ATTCTTTGWA C                                             21

(2) INFORMATION FOR SEQ ID NO:10:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

GCWACWTTAA ATGAAGTWTA T                                                    21

(2) INFORMATION FOR SEQ ID NO:11:

(i) SEQUENCE CHARACTERISTICS:
             (A) LENGTH: 21 bases
             (B) TYPE: nucleic acid
             (C) STRANDEDNESS: single
             (D) TOPOLOGY: linear (ii) MOLECULE TYPE: DNA (synthetic)

(xi) SEQUENCE DESCRIPTION: SEQ ID NO:11:

AATGAAGTWT ATCCWGTWAA T                                                    21

(2) INFORMATION FOR SEQ ID NO:12:

(i) SEQUENCE CHARACTERISTICS:
             (A) LENGTH: 38 bases
             (B) TYPE: nucleic acid
             (C) STRANDEDNESS: single
             (D) TOPOLOGY: linear (ii) MOLECULE TYPE: DNA (synthetic)

(xi) SEQUENCE DESCRIPTION: SEQ ID NO:12:

GCAAGCGGCC GCTTATGGAA TAAATTCAAT TYKRTCWA                                  38

(2) INFORMATION FOR SEQ ID NO:13:

(i) SEQUENCE CHARACTERISTICS:
             (A) LENGTH: 37 bases
             (B) TYPE: nucleic acid
             (C) STRANDEDNESS: single
             (D) TOPOLOGY: linear (ii) MOLECULE TYPE: DNA (synthetic)

(xi) SEQUENCE DESCRIPTION: SEQ ID NO:13:

AGACTGGATC CATGGCWACW ATWAATGAAT TATAYCC                                   37

(2) INFORMATION FOR SEQ ID NO:14:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: protein (xi) SEQUENCE DESCRIPTION: SEQ ID NO:14:

Glu Ser Lys Leu Lys Pro Asn Thr Arg Tyr
1               5                   10

(2) INFORMATION FOR SEQ ID NO:15:

(i) SEQUENCE CHARACTERISTICS:
             (A) LENGTH: 29 bases
             (B) TYPE: nucleic acid
             (C) STRANDEDNESS: single
             (D) TOPOLOGY: linear (ii) MOLECULE TYPE: DNA (synthetic)

(xi) SEQUENCE DESCRIPTION: SEQ ID NO:15:

TAACGTGTAT WCGSTTTTAA TTTWGAYTC                                            29

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Tyr Ile Asp Lys Ile Glu Phe Ile Pro
1               5

(2) INFORMATION FOR SEQ ID NO:17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

TGGAATAAAT TCAATTYKRT CWA                                                  23

(2) INFORMATION FOR SEQ ID NO:18:

(i) SEQUENCE CHARACTERISTICS:
        (A) LENGTH: 56 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:18:

ATGATTATTG ATTCTAAAAC AACATTACCA AGACATTCWT TAATWAATAC WATWAA              56

(2) INFORMATION FOR SEQ ID NO:19:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:19:

GAGTGGGAAG CAGATCTTAA TAATGCACAA TTAAGG                                    36

(2) INFORMATION FOR SEQ ID NO:20:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

ATACYCGATC GATATGATAR TCCGT                                                25

(2) INFORMATION FOR SEQ ID NO:21:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

CCCAATGTGA ATGTACTTTG CGC        23

(2) INFORMATION FOR SEQ ID NO:22:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

GACTGGATCC ATGAAAGAAW SWATWTATTA TAATGAAGA        39

(2) INFORMATION FOR SEQ ID NO:23:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

GGACCAGGAT TTACAGGAGG AGAT        24

(2) INFORMATION FOR SEQ ID NO:24:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

GGAATTCCTC ATGAAAGAGT CAATTTACTA C        31

(2) INFORMATION FOR SEQ ID NO:25:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

GTAAACATGT TCATACCACC TTTTTAA        27

(2) INFORMATION FOR SEQ ID NO:26:

(i) SEQUENCE CHARACTERISTICS:

(A) LENGTH: 34 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

GGTGATTTTA CACAAGGGGT AATGGGGTGG CATG                                  34

(2) INFORMATION FOR SEQ ID NO:27:

(i) SEQUENCE CHARACTERISTICS:
        (A) LENGTH: 3543 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ATGAATCCTT ATCAAAATAA AAATGAATAT GAAACATTAA ATGCTTCACA AAAAAAATTA      60

AATATATCTA ATAATTATAC AAGATATCCA ATAGAAAATA GTCCAAAACA ATTATTACAA     120

AGTACAAATT ATAAGATTG GCTCAATATG TGTCAACAGA ATCAGCAGTA TGGTGGAGAT      180

TTTGAAACTT TTATTGATAG TGGTGAACTC AGTGCCTATA CTATTGTAGT TGGGACCGTA     240

CTGACTGGTT TCGGGTTCAC AACACCCTTA GGACTTGCTT TAATAGGTTT TGGTACATTA     300

ATACCAGTTC TTTTTCCAGC CCAAGACCAA TCTAACACAT GGAGTGACTT TATAACACAA     360

ACTAAAAATA TTATAAAAAA AGAAATAGCA TCAACATATA TAAGTAATGC TAATAAAATT     420

TTAAACAGGT CGTTTAATGT TATCAGCACT TATCATAATC ACCTTAAAAC ATGGGAGAAT     480

AATCCAAACC CACAAAATAC TCAGGATGTA AGGACACAAA TCCAGCTAGT TCATTACCAT     540

TTTCAAAATG TCATTCCAGA GCTTGTAAAC TCTTGTCCTC CTAATCCTAG TGATTGCGAT     600

TACTATAACA TACTAGTATT ATCTAGTTAT GCACAAGCAG CAAACTTACA TCTGACTGTA     660

TTAAATCAAG CCGTCAAATT TGAAGCGTAT TTAAAAAACA ATCGACAATT CGATTATTTA     720

GAGCCTTTGC CAACAGCAAT TGATTATTAT CCAGTATTGA CTAAAGCTAT AGAAGATTAC     780

ACTAATTATT GTGTAACAAC TTATAAAAAA GGATTAAATT TAATTAAAAC GACGCCTGAT     840

AGTAATCTTG ATGGAAATAT AAACTGGAAC ACATACAATA CGTATCGAAC AAAAATGACT     900

ACTGCTGTAT TAGATCTTGT TGCACTCTTT CCTAATTATG ATGTAGGTAA ATATCCAATA     960

GGTGTCCAAT CTGAACTTAC TCGAGAAATT TATCAGGTAC TTAACTTCGA AGAAAGCCCC    1020

TATAAATATT ATGACTTTCA ATATCAAGAG GATTCACTTA CACGTAGACC GCATTTATTT    1080

ACTTGGCTTG ATTCTTTGAA TTTTTATGAA AAAGCGCAAA CTACTCCTAA TAATTTTTTC    1140

ACCAGCCATT ATAATATGTT TCATTACACA CTTGATAATA TATCCCAAAA ATCTAGTGTT    1200

TTTGGAAATC ACAATGTAAC TGATAAATTA AAATCTCTTG GTTTGGCAAC AAATATTTAT    1260

ATTTTTTAT TAAATGTCAT AAGCTTAGAT AATAAATATC TAAATGATTA TAATAATATT     1320

AGTAAAATGG ATTTTTTTAT AACTAATGGT ACTAGACTTT TGGAGAAAGA ACTTACAGCA    1380

GGATCTGGGC AAATAACTTA TGATGTAAAT AAAAATATTT TCGGGTTACC AATTCTTAAA    1440

CCAAGAGAGA ATCAAGCAAT CCCTACCCTT TTTCCAACAT ATGATAACTA TAGTCATATT    1500

TTATCATTTA TTAAAAGTCT TAGTATCCCT GCAACATATA AAACTCAAGT GTATACGTTT    1560

GCTTGGACAC ACTCTAGTGT TGATCCTAAA AATACAATTT ATACACATTT AACTACCCAA    1620

ATTCCAGCTG TAAAAGCGAA TTCACTTGGG ACTGCTTCTA AGGTTGTTCA AGGACCTGGT    1680

-continued

```
CATACAGGAG GGGATTTAAT TGATTTCAAA GATCATTTCA AAATTACATG TCAACACTCA    1740

AATTTTCAAC AATCGTATTT TATAAGAATT CGTTATGCTT CAAATGGAAG CGCAAATACA    1800

CGAGCTGTTA TAAATCTTAG TATCCCAGGG GTAGCAGAAC TGGGTATGGC ACTCAACCCC    1860

ACTTTTTCTG GTACAGATTA TACGAATTTA AAATATAAAG ATTTTCAGTA CTTAGAATTT    1920

TCTAACGAGG TGAAATTTGC TCCAAATCAA AACATATCTC TTGTGTTTAA TCGTTCGGAT    1980

GTATATACAA ACACAACAGT ACTTATTGAT AAAATTGAAT TTCTGCCAAT TACTCGTTCT    2040

ATAAGAGAGG ATAGAGAGAA ACAAAAATTA GAAACAGTAC AACAAATAAT TAATACATTT    2100

TATGCAAATC CTATAAAAAA CACTTTACAA TCAGAACTTA CAGATTATGA CATAGATCAA    2160

GCCGCAAATC TTGTGGAATG TATTTCTGAA GAATTATATC CAAAAGAAAA AATGCTGTTA    2220

TTAGATGAAG TTAAAAATGC GAAACAACTT AGTCAATCTC GAAATGTACT TCAAAACGGG    2280

GATTTTGAAT CGGCTACGCT TGGTTGGACA ACAAGTGATA ATATCACAAT TCAAGAAGAT    2340

GATCCTATTT TTAAAGGGCA TTACCTTCAT ATGTCTGGGG CGAGAGAAAT TGATGGTACG    2400

ATATTTCCGA CCTATATATT CCAAAAAATT GATGAATCAA AATTAAAACC GTATACACGT    2460

TACCTAGTAA GGGGATTTGT AGGAAGTAGT AAAGATGTAG AACTAGTGGT TTCACGCTAT    2520

GGGGAAGAAA TTGATGCCAT CATGAATGTT CCAGCTGATT TAAACTATCT GTATCCTTCT    2580

ACCTTTGATT GTGAAGGGTC TAATCGTTGT GAGACGTCCG CTGTGCCGGC TAACATTGGG    2640

AACACTTCTG ATATGTCGTA TTCATGCCAA TATGATACAG GAAAAAGCA TGTCGTATGT     2700

CAGGATTCCC ATCAATTTAG TTTCACTATT GATACAGGGG CATTAGATAC AAATGAAAAT    2760

ATAGGGGTTT GGGTCATGTT TAAAATATCT TCTCCAGATG GATACGCATC ATTAGATAAT    2820

TTAGAAGTAA TTGAAGAAGG GCCAATAGAT GGGGAAGCAC TGTCACGCGT GAAACACATG    2880

GAGAAGAAAT GGAACGATCA AATGGAAGCA AAACGTTCGG AAACACAACA AGCATATGAT    2940

GTAGCGAAAC AAGCCATTAA TGCTTTATTC ACAAATGTAC AAGATGAGGC TTTACAGTTT    3000

GATACGACAC TCGCTCAAAT TCAGTACGCT GAGTATTTGG TACAATCGAT TCCATATGTG    3060

TACAATGATT GGTTGTCAGA TGTTCCAGGT ATGAATTATG ATATCTATGT AGAGTTGGAT    3120

GCACGAGTGG CACAAGCGCG TTATTTGTAT GATACAAGAA ATATTATTAA AAATGGTGAT    3180

TTTACACAAG GGGTAATGGG GTGGCATGTA ACTGGAAATG CAGACGTACA ACAAATAGAT    3240

GGTGTTTCTG TATTGGTTCT ATCTAATTGG AGTGCTGGCG TATCTCAAAA TGTCCATCTC    3300

CAACATAATC ATGGGTATGT CTTACGTGTT ATTGCCAAAA AAGAAGGACC TGGAAATGGG    3360

TATGTCACGC TTATGGATTG TGAGGAGAAT CAAGAAAAAT TGACGTTTAC GTCTTGTGAA    3420

GAAGGATATA TTACGAAGAC AGTAGATGTA TTCCCAGATA CAGATCGTGT ACGAATTGAG    3480

ATAGGCGAAA CCGAAGGTTC GTTTTATATC GAAAGCATTG AATTAATTTG CATGAACGAG    3540

TGA                                                                 3543
```

(2) INFORMATION FOR SEQ ID NO:28:

(i) SEQUENCE CHARACTERISTICS:
        (A) LENGTH: 1180 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Met Asn Pro Tyr Gln Asn Lys Asn Glu Tyr Glu Thr Leu Asn Ala Ser

```
1               5                    10                   15
Gln Lys Lys Leu Asn Ile Ser Asn Asn Tyr Thr Arg Tyr Pro Ile Glu
                20                  25                  30
Asn Ser Pro Lys Gln Leu Leu Gln Ser Thr Asn Tyr Lys Asp Trp Leu
                35                  40                  45
Asn Met Cys Gln Gln Asn Gln Gln Tyr Gly Gly Asp Phe Glu Thr Phe
                50                  55                  60
Ile Asp Ser Gly Glu Leu Ser Ala Tyr Thr Ile Val Val Gly Thr Val
 65                 70                  75                  80
Leu Thr Gly Phe Gly Phe Thr Thr Pro Leu Gly Leu Ala Leu Ile Gly
                85                  90                  95
Phe Gly Thr Leu Ile Pro Val Leu Phe Pro Ala Gln Asp Gln Ser Asn
                100                 105                 110
Thr Trp Ser Asp Phe Ile Thr Gln Thr Lys Asn Ile Ile Lys Lys Glu
                115                 120                 125
Ile Ala Ser Thr Tyr Ile Ser Asn Ala Asn Lys Ile Leu Asn Arg Ser
                130                 135                 140
Phe Asn Val Ile Ser Thr Tyr His Asn His Leu Lys Thr Trp Glu Asn
145                 150                 155                 160
Asn Pro Asn Pro Gln Asn Thr Gln Asp Val Arg Thr Gln Ile Gln Leu
                165                 170                 175
Val His Tyr His Phe Gln Asn Val Ile Pro Glu Leu Val Asn Ser Cys
                180                 185                 190
Pro Pro Asn Pro Ser Asp Cys Asp Tyr Tyr Asn Ile Leu Val Leu Ser
                195                 200                 205
Ser Tyr Ala Gln Ala Ala Asn Leu His Leu Thr Val Leu Asn Gln Ala
                210                 215                 220
Val Lys Phe Glu Ala Tyr Leu Lys Asn Asn Arg Gln Phe Asp Tyr Leu
225                 230                 235                 240
Glu Pro Leu Pro Thr Ala Ile Asp Tyr Tyr Pro Val Leu Thr Lys Ala
                245                 250                 255
Ile Glu Asp Tyr Thr Asn Tyr Cys Val Thr Thr Tyr Lys Lys Gly Leu
                260                 265                 270
Asn Leu Ile Lys Thr Thr Pro Asp Ser Asn Leu Asp Gly Asn Ile Asn
                275                 280                 285
Trp Asn Thr Tyr Asn Thr Tyr Arg Thr Lys Met Thr Thr Ala Val Leu
                290                 295                 300
Asp Leu Val Ala Leu Phe Pro Asn Tyr Asp Val Gly Lys Tyr Pro Ile
305                 310                 315                 320
Gly Val Gln Ser Glu Leu Thr Arg Glu Ile Tyr Gln Val Leu Asn Phe
                325                 330                 335
Glu Glu Ser Pro Tyr Lys Tyr Asp Phe Gln Tyr Gln Glu Asp Ser
                340                 345                 350
Leu Thr Arg Arg Pro His Leu Phe Thr Trp Leu Asp Ser Leu Asn Phe
                355                 360                 365
Tyr Glu Lys Ala Gln Thr Thr Pro Asn Asn Phe Phe Thr Ser His Tyr
                370                 375                 380
Asn Met Phe His Tyr Thr Leu Asp Asn Ile Ser Gln Lys Ser Ser Val
385                 390                 395                 400
Phe Gly Asn His Asn Val Thr Asp Lys Leu Lys Ser Leu Gly Leu Ala
                405                 410                 415
Thr Asn Ile Tyr Ile Phe Leu Leu Asn Val Ile Ser Leu Asp Asn Lys
                420                 425                 430
```

-continued

```
Tyr Leu Asn Asp Tyr Asn Asn Ile Ser Lys Met Asp Phe Phe Ile Thr
        435                 440                 445

Asn Gly Thr Arg Leu Leu Glu Lys Glu Leu Thr Ala Gly Ser Gly Gln
    450                 455                 460

Ile Thr Tyr Asp Val Asn Lys Asn Ile Phe Gly Leu Pro Ile Leu Lys
465                 470                 475                 480

Pro Arg Glu Asn Gln Ala Ile Pro Thr Leu Phe Pro Thr Tyr Asp Asn
                485                 490                 495

Tyr Ser His Ile Leu Ser Phe Ile Lys Ser Leu Ser Ile Pro Ala Thr
            500                 505                 510

Tyr Lys Thr Gln Val Tyr Thr Phe Ala Trp Thr His Ser Ser Val Asp
        515                 520                 525

Pro Lys Asn Thr Ile Tyr Thr His Leu Thr Thr Gln Ile Pro Ala Val
    530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                565                 570                 575

Cys Gln His Ser Asn Phe Gln Gln Ser Tyr Phe Ile Arg Ile Arg Tyr
            580                 585                 590

Ala Ser Asn Gly Ser Ala Asn Thr Arg Ala Val Ile Asn Leu Ser Ile
        595                 600                 605

Pro Gly Val Ala Glu Leu Gly Met Ala Leu Asn Pro Thr Phe Ser Gly
    610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                645                 650                 655

Asn Arg Ser Asp Val Tyr Thr Asn Thr Val Leu Ile Asp Lys Ile
            660                 665                 670

Glu Phe Leu Pro Ile Thr Arg Ser Ile Arg Glu Asp Arg Glu Lys Gln
        675                 680                 685

Lys Leu Glu Thr Val Gln Gln Ile Ile Asn Thr Phe Tyr Ala Asn Pro
    690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Leu Tyr Pro Lys Glu
                725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
        755                 760                 765

Trp Thr Thr Ser Asp Asn Ile Thr Ile Gln Glu Asp Asp Pro Ile Phe
    770                 775                 780

Lys Gly His Tyr Leu His Met Ser Gly Ala Arg Glu Ile Asp Gly Thr
785                 790                 795                 800

Ile Phe Pro Thr Tyr Ile Phe Gln Lys Ile Asp Glu Ser Lys Leu Lys
                805                 810                 815

Pro Tyr Thr Arg Tyr Leu Val Arg Gly Phe Val Gly Ser Ser Lys Asp
            820                 825                 830

Val Glu Leu Val Val Ser Arg Tyr Gly Glu Glu Ile Asp Ala Ile Met
        835                 840                 845
```

-continued

```
Asn Val Pro Ala Asp Leu Asn Tyr Leu Tyr Pro Ser Thr Phe Asp Cys
    850                 855                 860

Glu Gly Ser Asn Arg Cys Glu Thr Ser Ala Val Pro Ala Asn Ile Gly
865                 870                 875                 880

Asn Thr Ser Asp Met Ser Tyr Ser Cys Gln Tyr Asp Thr Gly Lys Lys
                885                 890                 895

His Val Val Cys Gln Asp Ser His Gln Phe Ser Phe Thr Ile Asp Thr
                900                 905                 910

Gly Ala Leu Asp Thr Asn Glu Asn Ile Gly Val Trp Val Met Phe Lys
            915                 920                 925

Ile Ser Ser Pro Asp Gly Tyr Ala Ser Leu Asp Asn Leu Glu Val Ile
        930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
                965                 970                 975

Gln Ala Tyr Asp Val Ala Lys Gln Ala Ile Asn Ala Leu Phe Thr Asn
            980                 985                 990

Val Gln Asp Glu Ala Leu Gln Phe Asp Thr Thr Leu Ala Gln Ile Gln
        995                1000                1005

Tyr Ala Glu Tyr Leu Val Gln Ser Ile Pro Tyr Val Tyr Asn Asp Trp
    1010                1015                1020

Leu Ser Asp Val Pro Gly Met Asn Tyr Asp Ile Tyr Val Glu Leu Asp
1025                1030                1035                1040

Ala Arg Val Ala Gln Ala Arg Tyr Leu Tyr Asp Thr Arg Asn Ile Ile
                1045                1050                1055

Lys Asn Gly Asp Phe Thr Gln Gly Val Met Gly Trp His Val Thr Gly
            1060                1065                1070

Asn Ala Asp Val Gln Gln Ile Asp Gly Val Ser Val Leu Val Leu Ser
        1075                1080                1085

Asn Trp Ser Ala Gly Val Ser Gln Asn Val His Leu Gln His Asn His
    1090                1095                1100

Gly Tyr Val Leu Arg Val Ile Ala Lys Lys Glu Gly Pro Gly Asn Gly
1105                1110                1115                1120

Tyr Val Thr Leu Met Asp Cys Glu Glu Asn Gln Glu Lys Leu Thr Phe
                1125                1130                1135

Thr Ser Cys Glu Glu Gly Tyr Ile Thr Lys Thr Val Asp Val Phe Pro
            1140                1145                1150

Asp Thr Asp Arg Val Arg Ile Glu Ile Gly Glu Thr Glu Gly Ser Phe
        1155                1160                1165

Tyr Ile Glu Ser Ile Glu Leu Ile Cys Met Asn Glu
    1170                1175                1180
```

(2) INFORMATION FOR SEQ ID NO:29:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

CCAAGGGCGT TTTTACACAA GAAATTCTCG AGAC             34

-continued (2) INFORMATION FOR SEQ ID NO:30:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
ATGAATCCAT ATCAAAATAA GAATGAATAT GAAATATTCA ATGCTCCATC CAATGGTTTT      60

AGCAAGTCTA ATAACTATTC TAGATATCCA TTAGCAAATA AGCCAAATCA ACCACTGAAA     120

AACACGAATT ACAAGATTG GCTCAATGTG TGTCAAGATA ATCAACAATA TGGCAATAAT      180

GCGGGGAATT TTGTTAGTTC TGAAACTATT GTTGGAGTTA GTGCAGGTAT TATTGTAGTA     240

GGAACTATGT TAGGAGCTTT TGCTGCCCCT GTCTTAGCTG CAGGTATAAT ATCTTTTGGG     300

ACTTTGTTGC CGATCTTTTG GCAAGGATCT GACCCTGCAA ATGTTTGGCA GGATTTGTTA     360

AACATCGGAG GAAGGCCTAT ACAAGAAATA GATAAAAACA TAATTAATGT ACTAACTTCT     420

ATCGTAACAC CTATAAAAAA TCAACTTGAT AAATATCAAG AATTTTTCGA TAAATGGGAG     480

CCAGCACGTA CACACGCTAA TGCTAAAGCA GTACATGATC TCTTTACTAC CTTAGAACCT     540

ATAATAGATA AGATTTAGA TATGTTAAAA AATAATGCTA GCTATCGAAT ACCAACACTC      600

CCTGCATATG CACAAATAGC TACTTGGCAC TTGAATTTAT TAAAACATGC TGCTACCTAT     660

TACAATATAT GGCTGCAAAA TCAAGGTATA AATCCAAGTA CTTTCAATTC ATCTAATTAC     720

TATCAGGGCT ATTTAAAACG TAAAATACAA GAATATACTG ACTATTGTAT ACAAACGTAC     780

AATGCAGGAC TAACTATGAT TAGAACTAAT ACTAACGCAA CATGGAATAT GTATAATACT     840

TACCGTTTAG AAATGACTCT AACTGTGTTA GATCTTATTG CTATTTTTCC AAATTATGAC     900

CCAGAAAAAT ATCCAATAGG AGTTAAATCT GAACTTACCA GAGAAGTTTA TACGAATGTT     960

AATTCAGATA CATTTAGAAC CATAACAGAA CTAGAAAATG GATTAACTAG AAATCCTACA    1020

TTATTTACTT GGATAAACCA AGGGCGTTTT TACACAAGAA ATTCTCGAGA CATTCTTGAT    1080

CCTTATGATA TTTTTTCTTT TACAGGTAAC CAGATGGCCT TTACACATAC TAATGATGAT    1140

CGCAACATAA TCTGGGGAGC GGTTCATGGA CATATTATTT CTCAAGACAC ATCCAAAGTA    1200

TTTCCTTTTT ATAGAAACAA ACCTATTGAT AAGGTCGAAA TTGTCAGACA TAGAGAGTAC    1260

TCAGATATAA TATATGAAAT GATATTTTTT TCGAATAGCA GTGAAGTATT TCGATATTCA    1320

TCCAATTCAA CAATAGAAAA TAATTATAAA AGAACTGATT CTTATATGAT TCCAAAACAA    1380

ACATGGAAAA ATAAAGAATA TGGTCATACT CTATCGTATA TAAAAACTGA ATTATATA      1440

TTTTCAGTAG TTAGAGAAAG AAGAAGAGTT GCATTTAGTT GGACACATAC TAGTGTTGAT    1500

TTCCAAAATA CAATAGATTT AGATAACATC ACCCAAATCC ACGCTCTAAA AGCTTTGAAG    1560

GTAAGTTCTG ATTCGAAAAT TGTGAAAGGT CCTGGTCACA CAGGTGGAGA CTTGGTAATT    1620

CTTAAAGATA GTATGGATTT TAGAGTTAGA TTTTTAAAAA ATGTTTCTCG ACAATATCAA    1680

GTACGTATTC GTTATGCTAC TAATGCTCCA AAGACAACAG TATTCTTAAC CGGAATAGAT    1740

ACTATAAGTG TGGAGCTCCC TAGTACCACT TCCCGCCAAA ACCCAAATGC TACAGATTTA    1800

ACATATGCAG ATTTTGGATA TGTAACATTT CCAAGAACAG TTCCAAATAA ACATTTGAA     1860

GGAGAAGACA CTTTATTAAT GACCTTATAT GGTACACCAA ATCATTCATA TAATATATAT    1920

ATTGACAAAA TCGAATTTAT TCCAATCACT CAATCTGTAT TAGATTATAC AGAGAAGCAA    1980

AATATAGAAA AAACACAGAA AATAGTGAAT GATTTATTTG TTAATTAAAA CAAAGTTCTT    2040
```

ACTAAAAATAG ATAGTATGGC T                                                         2061

(2) INFORMATION FOR SEQ ID NO:31:

(i) SEQUENCE CHARACTERISTICS:
        (A) LENGTH: 686 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Met Asn Pro Tyr Gln Asn Lys Asn Glu Tyr Glu Ile Phe Asn Ala Pro
1               5                   10                  15

Ser Asn Gly Phe Ser Lys Ser Asn Asn Tyr Ser Arg Tyr Pro Leu Ala
            20                  25                  30

Asn Lys Pro Asn Gln Pro Leu Lys Asn Thr Asn Tyr Lys Asp Trp Leu
        35                  40                  45

Asn Val Cys Gln Asp Asn Gln Gln Tyr Gly Asn Asn Ala Gly Asn Phe
50                  55                  60

Val Ser Ser Glu Thr Ile Val Gly Val Ser Ala Gly Ile Ile Val Val
65                  70                  75                  80

Gly Thr Met Leu Gly Ala Phe Ala Ala Pro Val Leu Ala Ala Gly Ile
                85                  90                  95

Ile Ser Phe Gly Thr Leu Leu Pro Ile Phe Trp Gln Gly Ser Asp Pro
            100                 105                 110

Ala Asn Val Trp Gln Asp Leu Leu Asn Ile Gly Gly Arg Pro Ile Gln
        115                 120                 125

Glu Ile Asp Lys Asn Ile Ile Asn Val Leu Thr Ser Ile Val Thr Pro
130                 135                 140

Ile Lys Asn Gln Leu Asp Lys Tyr Gln Glu Phe Phe Asp Lys Trp Glu
145                 150                 155                 160

Pro Ala Arg Thr His Ala Asn Ala Lys Ala Val His Asp Leu Phe Thr
                165                 170                 175

Thr Leu Glu Pro Ile Ile Asp Lys Asp Leu Asp Met Leu Lys Asn Asn
            180                 185                 190

Ala Ser Tyr Arg Ile Pro Thr Leu Pro Ala Tyr Ala Gln Ile Ala Thr
        195                 200                 205

Trp His Leu Asn Leu Leu Lys His Ala Ala Thr Tyr Tyr Asn Ile Trp
210                 215                 220

Leu Gln Asn Gln Gly Ile Asn Pro Ser Thr Phe Asn Ser Ser Asn Tyr
225                 230                 235                 240

Tyr Gln Gly Tyr Leu Lys Arg Lys Ile Gln Glu Tyr Thr Asp Tyr Cys
                245                 250                 255

Ile Gln Thr Tyr Asn Ala Gly Leu Thr Met Ile Arg Thr Asn Thr Asn
            260                 265                 270

Ala Thr Trp Asn Met Tyr Asn Thr Tyr Arg Leu Glu Met Thr Leu Thr
        275                 280                 285

Val Leu Asp Leu Ile Ala Ile Phe Pro Asn Tyr Asp Pro Glu Lys Tyr
290                 295                 300

Pro Ile Gly Val Lys Ser Glu Leu Thr Arg Glu Val Tyr Thr Asn Val
305                 310                 315                 320

Asn Ser Asp Thr Phe Arg Thr Ile Thr Glu Leu Glu Asn Gly Leu Thr
                325                 330                 335
```

```
Arg Asn Pro Thr Leu Phe Thr Trp Ile Asn Gln Gly Arg Phe Tyr Thr
            340             345             350
Arg Asn Ser Arg Asp Ile Leu Asp Pro Tyr Asp Ile Phe Ser Phe Thr
        355             360             365
Gly Asn Gln Met Ala Phe Thr His Thr Asn Asp Asp Arg Asn Ile Ile
    370             375             380
Trp Gly Ala Val His Gly His Ile Ile Ser Gln Asp Thr Ser Lys Val
385             390             395                         400
Phe Pro Phe Tyr Arg Asn Lys Pro Ile Asp Lys Val Glu Ile Val Arg
            405             410             415
His Arg Glu Tyr Ser Asp Ile Ile Tyr Glu Met Ile Phe Phe Ser Asn
            420             425             430
Ser Ser Glu Val Phe Arg Tyr Ser Ser Asn Ser Thr Ile Glu Asn Asn
        435             440             445
Tyr Lys Arg Thr Asp Ser Tyr Met Ile Pro Lys Gln Thr Trp Lys Asn
    450             455             460
Lys Glu Tyr Gly His Thr Leu Ser Tyr Ile Lys Thr Asp Asn Tyr Ile
465             470             475             480
Phe Ser Val Val Arg Glu Arg Arg Val Ala Phe Ser Trp Thr His
            485             490             495
Thr Ser Val Asp Phe Gln Asn Thr Ile Asp Leu Asp Asn Ile Thr Gln
            500             505             510
Ile His Ala Leu Lys Ala Leu Lys Val Ser Ser Asp Ser Lys Ile Val
        515             520             525
Lys Gly Pro Gly His Thr Gly Gly Asp Leu Val Ile Leu Lys Asp Ser
    530             535             540
Met Asp Phe Arg Val Arg Phe Leu Lys Asn Val Ser Arg Gln Tyr Gln
545             550             555                         560
Val Arg Ile Arg Tyr Ala Thr Asn Ala Pro Lys Thr Thr Val Phe Leu
            565             570             575
Thr Gly Ile Asp Thr Ile Ser Val Glu Leu Pro Ser Thr Thr Ser Arg
            580             585             590
Gln Asn Pro Asn Ala Thr Asp Leu Thr Tyr Ala Asp Phe Gly Tyr Val
        595             600             605
Thr Phe Pro Arg Thr Val Pro Asn Lys Thr Phe Glu Gly Glu Asp Thr
    610             615             620
Leu Leu Met Thr Leu Tyr Gly Thr Pro Asn His Ser Tyr Asn Ile Tyr
625             630             635             640
Ile Asp Lys Ile Glu Phe Ile Pro Ile Thr Gln Ser Val Leu Asp Tyr
            645             650             655
Thr Glu Lys Gln Asn Ile Glu Lys Thr Gln Lys Ile Val Asn Asp Leu
        660             665             670
Phe Val Asn Asn Lys Val Leu Thr Lys Ile Asp Ser Met Ala
        675             680             685
```

MATERIALS AND METHODS FOR THE CONTROL OF CALLIPHORIDAE PESTS

CROSS-REFERENCE TO A RELATED APPLICATION

This is a divisional of application Ser. No. 08/856,226, filed May 14, 1997 U.S. Pat. No. 5,888,503; which is a divisional of application Ser. No. 08/249,780, filed May 26, 1994, now abandoned; which is a divisional of application Ser. No. 08/093,199, filed Jul. 15, 1993, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *san diego* (a.k.a. *B.t. tenebrionis*, a.k.a. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," Developments in *Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whitely [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. U.S. Pat. Nos. 4,797,276 and 4,853,331 disclose *B. thuringiensis* strain *san diego* (a.k.a. *B.t. tenebrionis*, a.k.a. M-7) which can be used to control coleopteran pests in various environments. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes. Certain *B.t.* isolates have been described that have activity against flies, Australian Patent Publication No. AU-B-27866/84. These isolates are not, however, those isolates disclosed and claimed herein. Many other patents have issued for new *B.t.* isolates and new uses of *B.t.* isolates. The discovery of new *B.t.* isolates and new uses of known *B.t.* isolates remains an empirical, unpredictable art.

The Calliphoridae family, together with the Sarcophagidae and the Oestridae families, contain the species responsible for the most important myiases of domestic animals and man. Myiasis is the infestation of living animals with the larvae of dipteran flies. Myiasis caused by members of the family Calliphoridae is commonly called "blowfly strike." The "blow" is the laying of the eggs by the fly at or near a strike site. The "strike" is the development of the eggs into maggots and the damage that this development causes at that site. Strikes are classified by the area of the body affected.

Blowfly myiasis primarily affects sheep; however, many other animals may be affected. Major species of blowflies include *Lucilia sericata* (greenbottles), *Phormia terraenovae* (blackbottles), *Calliphora erythrocephala* and *C. vomitoria* (bluebottles) in Europe. These flies are characterized by the color of the metallic sheen on their body sections. *Lucilia cuprina*, *L. caeser*, *L. illustris*, *Phormia regina*, *Calliphora stygia*, *C. australis*, *C. fallax*, *Chrysomyia albiceps*, *C. chlorophyga*, *C. micropogon*, and *C. rufifacies* are major species of blowflies in the tropics and subtropics.

The blowflies that attack sheep fall into two main categories:

(1) Primary flies, which are capable of initiating a strike on living sheep. These include Lucilia and Phormia spp. and some Calliphora spp.

(2) Secondary flies, which cannot initiate a strike, but attack an area already struck or otherwise damaged. They frequently extend the injury, rendering the strike one of great severity. Examples include many Calliphora spp. and, in warmer climates, Chrysomyia spp.

Eggs laid on the wool of sheep by primary flies, under favorable conditions, hatch within 12 hours. The hatched larvae migrate down the wool to the skin where the larvae lacerate the skin with their oral hooks and secrete proteolytic enzymes into the skin to establish the lesion. The larvae feed on the surrounding tissues, grow rapidly, and moult twice before becoming fully mature maggots. The maggots then drop to the ground and develop into mature flies. During the period of larval development, extensive tissue damage occurs, and the strike becomes available for the establishment of secondary infections or, worse, becomes an attractive site in which secondary blowflies may lay their eggs.

The irritation and distress caused by blowfly strikes are extremely debilitating, and sheep can rapidly lose condition. Where death occurs, it is often due to septicaemia. Affected sheep are anorexic, appear dull, and usually stay away from the main flock. Current methods of control are based primarily on the prophylactic treatment of sheep with insecticides. The problems associated with this are the relatively short period spent by the larvae on the sheep, the repeated infestations that occur throughout the season, and the rapidity with which severe damage occurs. Any insecticide used must therefore not only kill the larvae, but persist in the fleece. In this respect, the chlorinated hydrocarbon, dieldrin, proved particularly effective and gave protection for at least 20 weeks. However, this product has been largely withdrawn on safety grounds and replaced mainly by organophosphorus compounds, which have a persistence of 10–16 weeks unless resistance supervenes wherein this period becomes much shorter.

Application of these insecticides is made by plunge dipping or, more rarely in Europe, in a spray race or by jetting. In Europe, the high prevalence of body strike makes whole body protection necessary, and therefore the use of dips is more effective. In practice, an annual dip, usually in June, should give protection for the remainder of the fly season, but a second dipping in August may be necessary in order to ensure complete protection.

The name screw-worm is given to the larvae of certain species of Cochliomyia (syn. Callitroga) including *C. hominivorax* and *C. macellaria,* and to that of a single species of Chrysomyia, *C. bezziani,* which cause screw-worm myiasis in animals and occasionally man. Cochliomyia is found in the New World, while *C. bezziani* is confined to Africa and Asia.

The bluish-green flies have longitudinal stripes on the thorax and orange-brown eyes (Pl. IX). They occur primarily in tropical areas and lay their eggs on wounds, the larval stages characteristically feeding as a colony and penetrating the tissues creating a large and foul-smelling lesion. *C. hominivorax* was such a problem in the southern United States that a mass eradication campaign using biological control was undertaken. This involved the release of up to 1,000 male flies, sterilized by irradiation, per square mile. Since the female fly mates only once, control proved very successful except where the flies, which are capable of flying up to 200 miles, migrated from across the Mexican border.

Regular use of chemicals to control unwanted organisms can select for drug resistant strains. This has occurred in many species of economically important pests. Biological control programs circumvent the selection problem of drug resistance and are ecologically favored; however, as illustrated by the use in screw-worm control, can be limited by the biology of the fly. The development of drug resistance and the limitations of biological control programs necessitate a continuing search for new control agents having different modes of action.

At the present time there is a need to have more effective means to control these pests that cause considerable damage to susceptible hosts. Advantageously, such effective means would employ biological agents.

BRIEF SUMMARY OF THE INVENTION

The subject invention concerns novel materials and methods for controlling pests of the family Calliphoridae. The materials and methods of the subject invention result from the unexpected discovery that certain *B.t.* isolates have activity against these pests. Specifically exemplified herein is activity against screw-worms and the sheep blowfly.

More specifically, the methods of the subject invention use *B.t.* microbes, or variants thereof, and/or their toxins, to control Calliphoridae. Specific *B.t.* microbes useful according to the invention are *B.t.* PS123D1, *B.t.* PS71M3, *B.t.* PS63B, *B.t.* PS52A1, *B.t.* PS80JJ1, *B.t.* PS204G6, *B.t.* PS91C2, *B.t.* PS173A, *B.t.* PS31J2, *B.t.* PS201T6, *B.t.* PS86Q3, *B.t.* PS74G1, *B.t.* PS33F2, *B.t.* PS202U2, *B.t.* PS83E5, *B.t.* PS84C3, *B.t.* PS204C3, *B.t.* PS207B6, and *B.t.* PS211B2. Further, the subject invention includes the use of variants of the exemplified *B.t.* isolates which have substantially the same calliphorid-active properties as the specifically exemplified *B.t.* isolates. Such variants would include, for example, mutants. Procedures for making mutants are well known in the microbiological art. Ultraviolet light and nitrosoguanidine are used extensively toward this end.

The subject invention also includes the use of genes from the *B.t.* isolates of the invention which genes encode the calliphorid-active toxins.

Still further, the invention also includes the treatment of substantially intact *B.t.* cells, or recombinant cells containing the genes of the invention, to prolong the calliphorid activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE SEQUENCES

SEQ ID NO. 1 is the N-terminal amino acid sequence of 86Q3(a).

SEQ ID NO. 2 is the N-terminal amino acid sequence of 63B.

SEQ ID NO. 3 is the N-terminal amino acid sequence of 52A1.

SEQ ID NO. 4 is the N-terminal amino acid sequence of 33F2.

SEQ ID NO. 5 is an internal amino acid sequence for 63B(2).

SEQ ID NO. 6 is an oligonucleotide primer used according to the subject invention.

SEQ ID NO. 7 is an oligonucleotide primer used according to the subject invention.

SEQ ID NO. 8 is the forward oligonucleotide primer for 63B-A.

SEQ ID NO. 9 is the reverse oligonucleotide primer for 63B-INT.

SEQ ID NO. 10 is the oligonucleotide probe 33F2A.

SEQ ID NO. 11 is the oligonucleotide probe 33F2B.

SEQ ID NO. 12 is a reverse primer according to the subject invention.

SEQ ID NO. 13 is an oligonucleotide 5Q primer derived from the N-terminal amino acid sequence of SEQ ID NO. 1 (86Q3(a)).

SEQ ID NO. 14 is the amino acid sequence encoded by the oligonucleotide of SEQ ID NO. 15.

SEQ ID NO. 15 is a 3Q reverse oligonucleotide primer used according to the subject invention.

SEQ ID NO. 16 is the amino acid sequence encoded by the oligonucleotide of SEQ ID NO. 17.

SEQ ID NO. 17 is 3Q reverse oligonucleotide primer used according to the subject invention.

SEQ ID NO. 18 is the oligonucleotide probe 52A1-C.

SEQ ID NO. 19 is a forward oligonucleotide primer used according to the subject invention.

SEQ ID NO. 20 is a reverse oligonucleotide primer used according to the subject invention.

SEQ ID NO. 21 is an oligonucleotide probe used according to the subject invention.

SEQ ID NO. 22 is an oligonucleotide probe used according to the subject invention.

SEQ ID NO. 23 is the *B.t.* universal primer.

SEQ ID NO. 24 is a gene-specific primer used according to the subject invention.

SEQ ID NO. 25 is a promoter sequence-primer used according to the subject invention.

SEQ ID NO. 26 is an oligonucleotide primer used according to the subject invention.

SEQ ID NO. 27 is the nucleotide sequence encoding an approximately 130 kD *B.t.* toxin.

SEQ ID NO. 28 is the deduced amino acid sequence of the approximately 130 kD *B.t.* toxin encoded by SEQ ID NO. 27.

SEQ ID NO. 29 is an oligonucleotide probe used according to the subject invention.

SEQ ID NO. 30 is the nucleotide sequence encoding an approximately 77 kD *B.t.* toxin.

SEQ ID NO. 31 is the deduced amino acid sequence of the approximately 77 kD *B.t.* toxin encoded by SEQ ID NO. 30.

DETAILED DISCLOSURE OF THE INVENTION

The subject invention concerns the use of selected strains of *Bacillus thuringiensis* for the control of calliphorid pests.

Specific *Bacillus thuringiensis* isolates useful according to the subject invention have the following characteristics in their biologically pure form:

TABLE 1

Characteristics of *Bacillus thuringiensis* strains with sheep blowfly activity

| B.t. strain | Inclusion type | Approx. mol. wt. of protein | Serovar |
| --- | --- | --- | --- |
| PS123D1 | Amorphic | 133, 67, 27 | israelensis |
| PS71M3 | Amorphic | 142, 133, 67, 27 | morrisoni |
| PS63B | Amorphic | 84, 82, 78 | wuhanensis |
| PS52A1 | Multiple attached | 58, 45 | wuhanensis |
| PS80JJ1 | Multiple | 130, 90, 47, 37 | sotto |
| PS204G6 | Long amorphic | 23, 21 | wuhanensis |
| PS91C2 | Bipyramid | 130 | morrisoni |
| PS173A | Amorphic | 133, 67, 27 | israelensis |
| PS31J2 | Flat square & diamond | 64, 33 | morrisoni |
| PS201T6 | Bipyramid & elliptical | 133, 31 | neoleonensis |
| PS86Q3 | Long amorphic | 155, 135, 98, 58 | new serovar |
| PS74G1 | Amorphic | 140, 135, 112, 105, 63 | darmstadiensis |
| PS33F2 | Bipyramid | 140, 94 | wuhanensis |
| PS202U2 | Multiple attached | 58, 45 | wuhanensis |
| PS83E5 | Multiple | 42, 37 | wuhanensis |
| PS84C3 | Large amorphic | 70, 41, 36, 35 | entomocidus |
| PS204C3 | Multiple | 110, 105, 62, 45, 39 | wuhanensis |
| PS207B6 | Amorphic | 39, 29 | wuhanensis |
| PS211B2 | Large amorphic & ellipse | 83, 70, 41, 36, 35 | entomocidus |

*B.t.* isolates useful according to the subject invention have been deposited. Also deposited are recombinant microbes comprising the *B.t.* genes of interest.

TABLE 2

Deposit information for *B.t.* strains

| B.t. strain | Accession Number | Deposit date |
| --- | --- | --- |
| PS123D1 | NRRL B-21011 | October 13, 1992 |
| PS71M3 | NRRL B-18930 | December 27, 1991 |
| PS63B | NRRL B-18246 | July 28, 1987 |
| PS52A1 | NRRL B-18245 | July 28, 1987 |
| PS80JJ1 | NRRL B-18679 | July 17, 1990 |
| PS204G6 | NRRL B-18686 | July 17, 1990 |
| PS91C2 | NRRL B-18931 | December 27, 1991 |
| PS173A | NRRL B-21010 | October 13, 1992 |
| PS31J2 | NRRL B-21009 | October 13, 1992 |
| PS201T6 | NRRL B-18750 | January 9, 1991 |
| PS86Q3 | NRRL B-18765 | February 6, 1991 |
| PS74G1 | NRRL B-18397 | August 16, 1988 |
| PS33F2 | NRRL B-18244 | July 28, 1987 |
| PS202U2 | NRRL B-18832 | May 31, 1991 |
| PS83E5 | NRRL B-18782 | March 7, 1991 |
| PS84C3 | NRRL B-18399 | August 16, 1988 |
| PS204C3 | NRRL B-21008 | October 6, 1992 |
| PS207B6 | NRRL B-21007 | October 6, 1992 |
| PS211B2 | NRRL B-18921 | November 15, 1991 |
| E. coli NM522(pMYC2361) | NRRL B-21016N | December 17, 1992 |
| E. coli NM522(pMYC2357) | NRRL B-21017 | December 2, 1992 |
| E. coli NM522(pMYC2362) | NRRL B-21018 | December 2, 1992 |

The cultures are on deposit in the permanent collection of the Northern Research Laboratory, U.S. Department of Agriculture, Peoria, Ill., U.S.A.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Genes and toxins. The genes and toxins useful according to the subject invention include not only the full length sequences disclosed herein but also fragments of these sequences, or fusion proteins, which retain the characteristic pesticidal activity of the toxins specifically exemplified herein.

It should be apparent to a person skilled in this art that genes coding for calliphorid-active toxins can be identified and obtained through several means. The specific genes exemplified herein may be obtained from the isolates deposited at a culture depository as described above. These genes, or portions or variants thereof, may also be constructed synthetically, for example, by use of a gene machine. As used herein, the terms "variants" or "variations" of genes refer to nucleotide sequences which code for the same toxins or which code for equivalent toxins having calliphorid activity. As used herein, the term "equivalent toxins" refers to toxins having the same or essentially the same biological activity against calliphorid pests as the claimed toxins. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct within other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample have substantial homology. The probe's detectable label provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures.

These fragments and mutations, which retain the pesticidal activity of the exemplified toxins, would be within the scope of the subject invention. Also, because of the redundancy of the genetic code, a variety of different DNA sequences can encode the amino acid sequence disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining calliphorid activity are also included in this definition. As used herein, the phrase "calliphorid activity" includes activity against calliphorid larvae as well as other stages of development.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for variant toxins) having the same or essentially the same biological activity against calliphorids of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts. The toxin-encoding genes harbored by the isolates of the subject invention can be introduced into a wide variety of microbial, plant, or animal hosts. Expression of the toxin gene results, directly or indirectly, in the intracellular production and maintenance of the pesticide. With suitable microbial hosts, e.g., Pseudomonas, the microbes can be applied to the situs of calliphorids where they will proliferate and be ingested by the pest. The result is a control of this pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the pest environment. These microorganisms are selected so as to be capable of successfully competing in that environment with the wild-type microorganisms that are present. The microorganism host must also provide for stable maintenance and expression of the gene expressing the polypeptide pesticide, and, desirably, provide for improved protection of the pesticide from environmental degradation and inactivation.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques,* W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. The *B.t.* cells may be formulated in a variety of ways. In a preferred embodiment the *B.t.* cells or the toxin is applied as a drench. In a further embodiment of the invention, *B.t.* cells or toxin are presented to the fly in a "bait bin." Formulations applicable for use with these embodiments include wettable powders, granules or dusts, and mixtures with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The *B.t.* toxins of the invention can be administered as a liquid drench when used against calliphorids on sheep or other animals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight.

Where it is desired to administer the toxin compounds in a dry form, these forms are prepared by intimately and uniformly mixing the active ingredient with suitable finely divided diluents, fillers, disintegrating agents and/or binders such as starch, lactose, talc, magnesium stearate, vegetable gums and the like. Such formulations may be varied widely with respect to their total weight and content of the anti-parasitic agent, depending upon the factors such as the type of host animal to be treated, the severity and type of infection and the weight of the host.

The methods and compositions of the subject invention can be used to control calliphorids, which can parasitize vertebrates. Specifically, the invention can be used to control calliphorids in humans, livestock, domestic pets, and other animals. As used herein, the term "livestock" can include, for example, sheep, cattle, pigs, and goats. The methods and compositions of the subject invention may be used to control immature and adult calliphorids. The methods of control include, but are not limited to, direct application to the animal coat. The B.t. toxins described herein may be used alone, or in rotation or combination with other anti-calliphorid chemicals.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., wool, by spraying, dusting, sprinkling, or the like.

In a further embodiment of the invention, the B.t. cells or toxin are presented to the fly in a "bait bin." A bait bin comprises a large, covered bin containing an attractant, i.e., part of a carcass, to attract and "trap" the files. The flies are exposed to the toxin after being "trapped" within the bin. A bait bin is most effective when placed in areas where sheep are handled, such as in shearing sheds or yards. A bait bin should be left in position up to 48 hours after the sheep are removed from the area to mop up stray flies.

Mutants. Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (-). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *Bacillus thuringiensis* Isolates

A subculture of a B.t. isolate of the invention can be used to inoculate the following medium, a peptone, glucose, salts medium.

| | |
|---|---|
| Bacto Peptone | 7.50 g/l |
| Glucose | 1.00 g/l |
| $KH_2PO_4$ | 3.40 g/l |
| $K_2HPO_4$ | 4.35 g/l |
| Salt Solution | 5.00 ml/l |
| $CaCl_2$ Solution | 5.00 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hours.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Purification of Protein and Amino Acid Sequencing

The B.t. isolates PS86Q3, PS63B, PS52A1, and PS33F2 were cultured as described in Example 1. The parasporal inclusion bodies were partially purified by sodium bromide (28–38%) isopycnic gradient centrifugation (Pfannenstiel, M. A., E. J. Ross, V. C. Kramer, K. W. Nickerson [1984] *FEMS Microbiol. Lett.* 21:39). The proteins were bound to PVDF membranes (Millipore, Bedford, Mass.) by western blotting techniques (Towbin, H., T. Staehlelin, K. Gordon [1979] *Proc. Natl. Acad Sci. USA* 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] *Meth. Enzymol.* 91:399). The sequences obtained were:

86Q3(a): M A T I N E L Y P N V P Y N V L (SEQ ID NO. 1)
63B: Q L Q A Q P L I P Y N V L A (SEQ ID NO. 2)
52A1: M I I D S K T T L P R H S L I N T (SEQ ID NO. 3)
33F2: A T L N E V Y P V N (SEQ ID NO. 4)

In addition, internal amino acid sequence data were derived for 63B. The toxin protein was partially digested with *Staphylococcus aureus* V8 protease (Sigma Chem. Co., St. Louis, Mo.) essentially as described (Cleveland, D. W., S. G. Fischer, M. W. Kirschner, U. K. Laemmli [1977] *J. Biol. Chem.* 252:1102). The digested material was blotted onto PVDF membrane and a ca. 28 kDa limit peptide was selected for N-terminal sequencing as described above. The sequence obtained was:

63B(2) V Q R I L D E K L S F Q L I K (SEQ ID NO.5)

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from calliphoricidal B.t. isolates. RFLP analysis of restricted total cellular DNA using radiolabeled oligonucleotide probes has elucidated different genes or gene fragments.

EXAMPLE 3

Restriction Fragment Length Polymorphism (RFLP) Analysis of δ-Endotoxin Genes From *Bacillus thuringiensis* Strain PS80JJ1

Total cellular DNA was prepared from *Bacillus thuringiensis* (B.t.) cells grown to an optical density, at 600 nm, of 1.0. Cells were pelleted by centrifugation and resuspended in protoplast buffer (20 mg/ml lysozyme in 0.3 M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform(1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An approximately 700–800 bp DNA fragment from a novel PS80JJ1 130 kDa toxin gene was obtained by polymerase chain reaction (PCR) amplification using PS80JJ1 cellular DNA and the following primers:

5Q GGACCAGGAT TTACAGG(T or A)GG (A or G)(A or G)A 3Q (SEQ ID NO. 6)

5Q TAACGTGTAT (A or T)CG(C or G)TTTTAA TTT(T or A)GA(C or T)TC 3Q (SEQ ID NO. 7)

This DNA fragment was cloned into pBluescript S/K (Stratagene, LaJolla, Calif.) and partially sequenced by dideoxynucleotide DNA sequencing methodology (Sanger et al. [1977] *Proc. Natl. Acad. Sci. USA* 74:5463–5467) using Sequenase (USBiochemical, Cleveland, Ohio). DNA sequences unique to at least one PS80JJ1 toxin gene were identified by computer comparison with other known δ-endotoxin genes.

The 700–800 bp DNA fragment was radiolabled with $^{32}$P and used in standard hybridizations of Southern blots of PS80JJ1 total cellular DNA. Hybridizing bands included an approximately 1.8 kbp EcoRI fragment and an approximately 9.5 kbp HindIII fragment. These hybridizing DNA bands contain toxin genes or restriction fragments of toxin genes from PS80JJ1.

EXAMPLE 4

Molecular Cloning of a Gene Encoding a Toxin from *Bacillus thuringiensis* Strain PS63B Example 2 shows the aminoterminal and internal polypeptide sequences of the 63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5Q end of the gene:

63B-A—5Q CAA(T or C)TACAAG C(A or T)CAACC 3Q (SEQ ID NO. 8)

The sequence of the reverse primer (63B-INT) was complementary to the inverse of the internal predicted DNA sequence:

63B-INT—5Q TTCATCTAAA ATTCTTTG(A or T)A C 3Q (SEQ ID NO. 9)

These primers were used in standard polymerase chain reactions (Cetus Corporation) to amplify an approximately 460 bp fragment of the 63B toxin gene for use as a DNA cloning probe. Standard Southern blots of total cellular DNA from 63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis* (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH 8.0) and lysozyme at a concentration of 20 mg/ml. The protoplasts were ruptured by addition of ten volumes of 0.1 M NaCl, 0.1 M Tris-HCl pH 8.0, and 0.1% SDS. The cellular material was quickly frozen at −70° C. and thawed to 37° C. twice. The supernatant was extracted twice with phenol/chloroform(1:1). The nucleic acids were precipitated with ethanol. To remove as much RNA as possible from the DNA preparation, RNase at final concentration of 200 μg/ml was added. After incubation at 37° C. for 1 hour, the solution was extracted once with phenol/chloroform and precipitated with ethanol.

A gene library was constructed from 63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (Promega). The packaged phage were plated on *E. coli* KW251 cells (Promega) at a high titer and screened using the radiolabeled approximately 430 bp fragment probe amplified with the 63B-A and 63B internal primers (SEQ ID NOS. 8 and 9, respectively) by polymerase chain reaction. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis, T., E. F. Fritsch, J. Sambrook [1982] *Molecular Cloning: A Laboratory Manual,* Cold Spring Harbor Laboratory, New York). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBlueScript S/K [Stratagene, San Diego, Calif.] and the replication origin from a resident *B.t.* plasmid [Lereclus, D. et al. (1989) *FEMS Microbiol. Lett.* 60:211–218]). The ligation mix was introduced by transformation into competent *E. coli* NM522 cells (ATCC 47000) and plated on LB agar containing ampicillin (100 μg/ml), isopropyl-β-D-thiogalactoside (IPTG) (2%), and 5-bromo-4-chloro-3-indolyl-β-D-galactoside (XGAL) (2%). White colonies, with putative restriction fragment insertions in the β-galactosidase gene of pHTBlueII, were subjected to standard rapid plasmid purification procedures (Maniatis et al., supra). Plasmids were analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 5
Molecular Cloning of a Toxin Gene From *B.t.* PS33F2 and Transformation into *Escherichia coli*

Total cellular DNA was prepared from *Bacillus thuringiensis* PS33F2 (*B.t.* PS33F2) as described above in Example 3.

Plasmid DNA was extracted from protoplasts prepared by incubation of cells for 1 hour at 37° C. in protoplast buffer (20 mg/ml lysozyme in 0.3 M sucrose, 25 mM Tris-HCl [pH 8.0], 25 mM EDTA). Protoplasts were lysed by the addition of nine volumes of a solution of 10 mM Tris-Cl, 1 mM EDTA, 0.085 N NaOH, 0.1% SDS, pH 8.0. SDS was added to 1% final concentration to complete lysis. One-half volume of 3 M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}$P-labelled oligonucleotide probes designed to the N-terminal amino acid sequence disclosed in Example 2.

Probe 33F2A: 5Q GC(A or T)AC(A or T)TTAA ATGAAGT(A or T)TA T 3Q (SEQ ID NO. 10)

Probe 33F2B: 5Q AATGAAGT(A or T)T ATCC(A or T)GT(A or T)AA T 3Q (SEQ ID NO. 11)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the 33F2 toxin gene. The sequence of the reverse primer was:

5Q GCAAGCGGCC GCTTATGGAA TAAATTCAAT T(C or T)(T or G)(A or G)TC(T or A)A 3Q (SEQ ID NO. 12).

A gene library was constructed from 33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an *E. coli/B. thuringiensis* shuttle vector comprised of pBluescript S/K [Stratagene] and the replication origin from a resident *B.t.* plasmid (Lereclus et al., supra]). The ligation mixture was transformed into frozen, competent NM522 cells (ATCC 47000). Transformants were plated on LB agar containing ampicillin, IPTG, and XGAL. Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding pesticidal proteins.

Plasmid pMYC2316 was introduced into the acrystalliferous (Cry-) *B.t.* host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (Pfannenstiel et al., supra).

EXAMPLE 6
Molecular Cloning and Expression of a Toxin Gene from *B.t.* Isolate PS86Q3

Total cellular DNA was prepared from *Bacillus thuringiensis* PS86Q3 (*B.t.* PS86Q3) as disclosed above in Example 3.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the toxin protein was used as a 5Q primer. The sequence of this oligonucleotide is:

5Q-AGACTGGATC CATGGC(A or T)AC(A or T) AT(A or T)AATGAAT TATA(T or C)CC-3Q (SEQ ID NO. 13).

An oligonucleotide coding for the amino acid sequence "ESKLKPNTRY" (SEQ ID NO. 14) can be used as the reverse 3Q primer. The sequence of this oligonucleotide can be: "5Q-TAACGTGTAT (A or T)CG(C or G)TTTTAA TTT(T or A)GA(C or T)TC-3Q" (SEQ ID NO. 15).

The oligonucleotide coding for the amino acid sequence "YIDKIEFIP" (SEQ ID NO. 16) was also used as a reverse 3Q primer in conjunction with the above mentioned 5Q primer. The sequence of the reverse primer can be: "5Q-TGGAATAAAT TCAATT(C or T)(T or G)(A or G)T C(T or A)A-3Q" (SEQ ID NO. 17).

Amplification with the 5Q primer and SEQ ID NO. 15 generates an approximately 2.3 kbp DNA fragment and an approximately 4.3 kbp DNA fragment. Amplification with the 5Q primer and SEQ ID NO. 17 generates an approximate 1.8 kbp DNA fragment and an approximately 3.7 kbp DNA fragment. The approximately 2.3 kbp fragment was radiolabeled with $^{32}$P and used as a hybridization probe to generate restriction fragment polymorphism (RFLP) patterns and to screen recombinant phage libraries.

A Southern blot of total cellular DNA digested with EcoRV was probed with the radiolabeled 2.3 kbp probe described above. The resultant RFLP includes 9.5 kbp, 6.4 kbp, and 4.5 kbp hybridizing fragments.

A gene library was constructed from PS86Q3 total cellular DNA partially digested with NdeII and size fractioned by gel electrophoresis. The 9–23 kb region of the gel was excised and the DNA was electroeluted and then concentrated using an Elutip-D ion exchange column (Schleicher and Schuel, Keene, N.H.). The isolated NdeII fragments were ligated into BamHI-digested LambdaGem-11 (Promega). The packaged phage were plated on *E. coli* KW251 cells (Promega) at a high titer and screened using the radiolabeled probe described above. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBluescript S/K [Stratagene, San Diego, Calif.]) and the replication origin from a resident *B.t.* plasmid (Lereclus et al., supra). The ligation mix was introduced by transformation into competent *E. coli* NM522 cells (ATCC 47000) and plated on LB agar containing ampicillin, IPTG, and XGAL. White colonies, with putative restriction fragment insertions in the β-galactosidase gene of pHTBlueII, were subjected to standard rapid plasmid purification procedures (Maniatis et al., supra). Plasmid DNA was analyzed by SalI digestion and agarose gel electrophoresis. The desired plasmid construct, pMYC1647, contains an approximately 12 kb SalI insert. Plasmid pMYC1647 was introduced by electroporation into an acrystalliferous (Cry⁻) *B.t.*, HD-1 CryB (A. I. Aronson, Purdue University) host to yield MR515, a recombinant *B.t.* clone of 86Q3(a). Expression of an approximately 155 kDa protein was verified by SDS-PAGE. Spores and crystals can be removed from broth cultures and used for determination of pesticidal activity.

EXAMPLE 7

Molecular Cloning and Expression of a Toxin Gene From *Bacillus thuringiensis* Strain PS52A1

Total cellular DNA was prepared from *Bacillus thuringiensis* PS52A1 (*B.t.* PS52A1) as disclosed above in Example 3.

RFLP analyses were performed by standard hybridization of Southern blots of PS52A1 DNA with a $^{32}P$-labeled oligonucleotide probe designed from the N-terminal amino acid sequence disclosed in Example 2. The sequence of this probe is:

5Q ATGATTATTG ATTCTAAAAC AACATTACCA AGACAT-TC(A or T)T TAAT(A or T)AATAC (A or T)AT(A or T)AA 3Q (SEQ ID NO. 18)

This probe was designated 52A1-C. Hybridizing bands included an approximately 3.6 kbp HindIII fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega). Recombinant phage were packaged and plated on *E. coli* KW251 cells (Promega). Plaques were screened by hybridization with the radiolabeled 52A1-C oligonucleotide probe disclosed above. Hybridizing phage were plaque-purified and used to infect liquid cultures of *E. coli* KW251 cells for isolation of phage DNA by standard procedures (Maniatis et al., supra). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+SalI-digested pHTBlueII (an *E. coli*/*B. thuringiensis* shuttle vector comprised of pBluescript S/K [Stratagene] and the replication origin from a resident *B.t.* plasmid [Lereclus et al., supra]). The ligation mix was used to transform frozen, competent *E. coli* NM522 cells (ATCC 47000). Transformants were plated on LB agar containing ampicillin, IPTG, and XGAL. Plasmids were purified from putative recombinants by alkaline lysis (Maniatis et al., supra) and analyzed by electrophoresis of EcoRI and SalI digests on agarose gels. The desired plasmid construct, pMYC2321 contains a toxin gene that is novel compared to the maps of other toxin genes.

Plasmid pMYC2321 was introduced into an acrystalliferous ($Cry^-$) *B.t.* host by electroporation. Expression of an approximately 55–60 kDa crystal protein was verified by SDS-PAGE analysis.

EXAMPLE 8

Molecular Cloning and Expression of a Toxin Gene from *Bacillus thuringiensis* Strain PS91C2

Total cellular DNA was prepared from *Bacillus thuringiensis* PS91C2 (*B.t.* PS91C2) as disclosed above in Example 3.

A 1.58 kbp fragment of the novel 130 kDa toxin gene was obtained by polymerase chain reaction (PCR) amplification from PS91C2 cellular DNA using the following primers: "Forward" 5Q-GAGTGGGAAGCAGATCTTAATAATGCACAATTAAGG-3Q (SEQ ID NO. 19); "Reverse" 5Q-ATAC(C or T)CGATC GATATGATA(G or A) TCCGT-3Q (SEQ ID NO.20). This DNA fragment was cloned into pBluescriptS/K (Stratagene, La Jolla, Calif.) and the DNA sequence determined by dideoxynucleotide sequencing methodology (Sanger et al., supra) using Sequenase (US Biochemicals, Cleveland, Ohio). DNA sequences that were unique were identified by computer comparison with other toxin genes. An oligonucleotide probe with the following sequence was synthesized: 5Q-CCCAATGTGA ATG-TACTTTG CGC-3Q (SEQ ID NO.21). This probe was radiolabelled with $^{32}P$ and used in standard hybridizations of Southern blots of PS91C2 total cellular DNA. Hybridizing bands included an approximately 7.5 kbp HindIII fragment.

A gene library was constructed from PS91C2 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with each of the respective probes described above. Hybridizing phage were plaque purified and used to infect liquid cultures of *E. coli* KW251 cells for isolation of DNA by standard procedures (Maniatis et al., supra).

For subcloning the gene encoding the 130 kDa toxin, preparative amounts of phage DNA were digested with SauI and electrophoresed on an agarose gel. The approximately 8 kbp bad containing the toxin gene was excised from the gel electroeluted from the gel slice, and purified by ion exchange chromatography as described above. The purified DNA insert was ligated into XhoI-digested pHTBlueII (an *E. coli*/*B. thuringiensis* shuttle vector comprised of pBluescript S/K (Stratagene, La Jolla, Calif.) and the replication origin from a resident B.t. plasmid (Lereclus et al., supra). The ligation mix was used to transform frozen, competent E. coli NM522 cells (ATCC 47000). β-galactosidase transformants were screened by restriction digestion of alkaline lysate plasmid minipreps as above. The desired plasmid construct, pMYC2361, contains a toxin gene that is novel compared to other toxin genes containing insecticidal proteins.

pMYC2361 was introduced into the acrystalliferous (Cry⁻) B.t. host. CryB (A. Aronson, Purdue University, West Lafayette, Ind.), by electroporation. Expression of the 130 kDa toxin was demonstrated by SDS-PAGE analysis. NaBr-purified crystals were prepared (Pfannenstiel et al., supra).

EXAMPLE 9
Molecular Cloning and Expression of Toxin Genes from *Bacillus thuringiensis* Strain PS201T6

Total cellular DNA was prepared from *Bacillus thuringiensis* PS201T6 (*B.t.* PS201T6) as described above in Example 3.

RFLP analyses were performed by standard hybridization of Southern blots of PS201T6 DNA digested with various restriction endonucleases. An oligonucleotide probe deduced from the amino acid sequence of the 30 kDa toxin was used to detect the gene encoding this polypeptide. The sequence of this probe was: 5Q-GACTGGATCC ATGAAAGAA(T or A)(G or C)(T or A)AT(T or A)TATTA TAATGAAGA-3Q (SEQ ID NO. 22). This probe was mixed at four positions and contained a 5Q BamHI cloning site. Hybridizing bands included an approximately 4.0 kbp EcoRI fragment and an approximately 2.7 kbp EcoRV fragment.

A 285 bp probe for detection of the 130 kDa toxin gene was obtained by polymerase chain reaction (PCR) amplification from 201T6 cellular DNA using the *B.t.* universal forward and YIDKIEFIP reverse oligonucleotide primers (SEQ ID NOS. 23 and 17, respectively). The sequence of the *B.t.* universal primer is: 5Q-GGACCAGGAT TACAG-GAGG AGAT-3Q (SEQ ID NO. 23). The amplified DNA fragment was radiolabelled with ³²P-dATP using a BMB (Indianapolis, Ind.) random priming kit. Southern blot analyses of PS201T6 DNA with this probe revealed hybridizing bands that included an approximately 9.3 kbp HindIII fragment and two EcoRI fragments approximately 1.8 and 4.5 kbp in size.

A gene library was constructed from PS201T6 DNA partially digested with Sau3A. Partial restriction digests were fractionated by agarose gel electrophoresis. DNA fragments 9.3 to 23 kbp in size were excised from the gel, electroeluted from the gel slice, purified on an Elutip D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinant phage were packaged and plated on *E. coli* KW251 cells. Plaques were screened by hybridization with each of the respective probes described above. Hybridizing phage were plaque purified and used to infect liquid cultures of *E. coli* KW251 cells for isolation of DNA by standard procedures (Maniatis et al., supra).

For subcloning the gene encoding the 30 kDa toxin gene, preparative amounts of phage DNA were digested with EcoRI and electrophoresed on an agarose gel. The approximately 4.5 kbp band containing the toxin gene was excised from the gel electroeluted from the gel slice, and purified by ion exchange chromatography as above. The purified DNA insert was ligated into EcoRI-digested pBluescript K/S (Stratagene, La Jolla, Calif.). The ligation mix was used to transform frozen, competent *E. coli* NM522 cells (ATCC 47000). Transformants were plated on LB agar containing 100 μg/ml ampicillin, 1 mM IPTG, and 0.5 mM XGAL. Plasmids were purified from putative recombinants by alkaline lysis (Maniatis et al., supra) and analyzed by restriction endonuclease digestion and agarose gel electrophoresis. The desired plasmid construct pMYC2357 contains a toxin gene that is novel compared to other toxin genes encoding insecticidal proteins.

The gene encoding the 30 kDa was expressed under control of the p52A1 promoter and ribosome binding site in the vector, pBClac (an *E. coli*/*B. thuringiensis* shuttle vector comprised of the replication origin from pBC16 (Bernhard, K. et al. [1978] *J. Bacteriol.* 133:897–903) and pUC19 (Yanisch-Perron, C. et al. [1985] *Gene* 33:103–119). The 30 kDa open reading frame and 3Q flanking sequences were amplified by PCR using a forward oligonucleotide complementary to the 5Q end of the gene and a reverse oligonucleotide complementary to the T7 promoter region of pBluescript. The sequence of the gene-specific primer was: 5Q-GGAATTCCTC ATG AAA GAG TCA ATT TAC TAC A-3Q (SEQ ID NO. 24). This primer contained a 5Q BspHI cloning site. The p52A1 promoter/rbs sequences were amplified using a promoter-specific primer and a vector primer from pMYC2321. The sequence of promoter-specific primer was 5Q-GTAAACATGT TCATACCACC TTTTTAA-3Q (SEQ ID NO. 25). This primer contained a 5Q AflIII cloning site. The p52A1 promoter fragment (digested with BamHI and AflIII), the 30 kDa toxin gene fragment (digested with BspHI and SalI) and pBClac (digested with BamHI and SalI) were ligated together to generate pMYC2358. This construct was introduced into the acrystalliferous (Cry⁻) *B.t.* host, CryB (A. Aronson, Purdue University, West Lafayette, Ind.) by electroporation. Expression of the 30 kDa toxin was demonstrated by SDS-PAGE analysis. NaBr-purified crystals were prepared (Pfannenstiel et al., supra).

For subcloning the 130 kDa toxin, preparative amounts of phage DNA were digested with SalI and electrophoresed on an agarose gel. The approximately 12.8 kbp band containing the toxin gene was excised from the gel, electroeluted from the gel slice, and purified by ion exchange chromatography as described above. The purified DNA insert was ligated into an XhoI-digested pHTBlueII (an *E. coli*/*B. thuringiensis* shuttle vector comprised of pBluescript S/K (Stratagene, La Jolla, Calif.) and the replication origin from a resident *B.t.* plasmid (Lereclus et al., supra). The ligation mix was used to transform frozen, competent *E. coli* NM522 cells (ATCC 47000). β-galactosidase transformants were screened by restriction digestion of alkaline lysate plasmid minipreps as above. The desired plasmid construct, pMYC2362, contains a toxin gene that is novel compared to other toxin genes encoding pesticidal proteins.

pMYC2362 was introduced into the acrystalliferous (Cry⁻) *B.t.* host, CryB (A. Aronson, Purdue University, West Lafayette, Ind.), by electroporation. Expression of the 130 kDa toxin was demonstrated by SDS-PAGE analysis.

EXAMPLE 10
Cloning of ≈130 kDa Toxin Gene from Isolate *B.t.* PS71M3 and Transformation into *Escherichia coli*

Total cellular DNA was prepared from *B.t.* cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH 8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform(1:1). The DNA was precipitated with ethanol and purified by isopycnic banding on a cesium gradient.

Total cellular DNA from B.t. PS71M3 was digested with EcoRV and separated by electrophoresis on a 0.8% (w/v) Agarose-TAE (50 mM Tris-Cl, 20 mM NaOAc, 2.5 mM EDTA, pH 8.0) buffered gel. A Southern blot of the gel was hybridized with a [$^{32}$P] radiolabeled probe. The sequence of the oligonucleotide is GGTGATTTTA CACAAGGGGT AATGGGGTGG CATG (SEQ ID NO. 26). Results showed that the hybridizing fragments of B.t. PS71M3 are 4.8 kb, 4.0 kb, and 3.8 kb in size.

A library was constructed from B.t. PS71M3 total cellular DNA partially digested with Sau3A and size fractionated by electrophoresis. The 9 to 23 kb region of the gel was excised and the DNA was electroeluted and then concentrated using an Elutip ion exchange column (Scleicher and Schuel, Keene, N.H.). The isolated Sau3A fragments were ligated into LambdaGem-11 (Promega). The packaged phage were plated on KW251 E. coli cells (Promega) at a high titer and screened using the radiolabeled synthetic oligonucleotide as a nucleic acid hybridization probe. Hybridizing plaques were purified and rescreened at a lower plaque density. Single isolated purified plaques that hybridized with the probe were used to infect KW251 E. coli cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac. The ligation mix was introduced by transformation into NM522 competent E. coli cells and plated on LB agar containing ampicillin, IPTG and XGAL. White colonies, with putative insertions in the β-galactosidase gene of pBClac, were subjected to standard rapid plasmid purification procedures to isolate the desired plasmid. The selected plasmid was named pMYC1625 and contains an 8.0 kb SalI insert.

The toxin gene was sequenced by the standard Sanger dideoxy chain termination method using oligonucleotide primers made to the B.t. i. cryIVA gene and by "walking" with primers made to the sequence of the new toxin gene. Sequence analysis of the toxin gene revealed that it encodes a protein of 134,934 daltons, deduced from the DNA sequence. The nucleotide and deduced amino acid sequences are shown in SEQ ID NOS. 27 and 28, respectively.

Plasmid pMYC1625 was introduced into a cured, acrystalliferous(Cry$^-$) B.t. host by electroporation. Expression of an ≈130 kD protein was verified by SDS-PAGE. Spores and crystals were used for the determination of toxicity to calliphorids.

The pBClac shuttle vector was constructed by fusing plasmids pBC16-1 (Bacillus Genetic Stock Center, Ohio State University, Department of Biochemistry, Columbus, Ohio) and pUC19 (New England Biolabs). The pBC16-1 plasmid was digested with EcoRI and the 5Q overhangs were filled in with deoxynucleotides(dATP, dCTP, dGTP, and dTTP) by Klenow enzyme (New England Biolabs). An SpeI restriction site was added by ligation of oligonucleotide linkers forming pBC16-1SpeI. In the same manner as above, an NheI restriction site was added to pUC19 at the Eco0109 site forming pUC19NheI. The pBC16-1SpeI plasmid was digested with SpeI and the pUC19NheI plasmid was digested with NheI, creating complementary cohesive ends that were ligated together to form the pBClac shuttle vector.

The plasmid containing the B.t. toxin gene can be removed from the transformed host microbe by use of standard well-known procedures. For example, the host microbe can be subjected to cleared lysate isopycnic density gradient procedures, and the like, to recover the desired plasmid.

The above gene can also be isolated from B.t. PS71M3-69 by the same procedures.

EXAMPLE 11
Cloning of ≈77 kDa Toxin Gene From Isolate B.t. PS71M3 and Transformation into Escherichia coli As described As described in Example 10, total cellular DNA was prepared. Total cellular DNA from B.t. PS71M3 was digested with EcoRV and separated by electrophoresis on a 0.8% (w/v) agarose-TAE(50 mM Tris-HCl, 20 mM NaOAc, 2.5 mM EDTA, ph=8.0) buffered gel. A Southern blot of the gel was hybridized with a [$^{32}$P]-radiolabeled oligonucleotide probe. The sequence of the oligonucleotide is CCAAGGGCGT TTTTACACAA GAAATTCTCG AGAC (SEQ ID NO. 29). Results showed that the hybridizing fragments of B.t. PS71M3 are approximately 14.0 kb and 2.9 kb in size.

A library was constructed as described in Example 10. White colonies, with putative insertions in the β-galactosidase gene of pBClac, were subjected to standard rapid plasmid purification procedures to isolate the desired plasmid. The selected plasmid was named pMYC1636 and contains an approximately 15 kb SalI insert.

The restriction map of the cloned insert indicates that the toxin gene is novel compared to the maps of other toxin genes encoding calliphoricidal proteins.

The toxin gene was sequenced by the standard dideoxy chain termination method using oligonucleotide primers made to the B.t.i. cryIVC gene and by "walking" with primers made to the sequence of the new toxin gene. Sequence analysis of the toxin gene revealed an open reading frame that is ≈95% homologous to the cryIVC gene, and encodes a protein of 77,798 daltons, deduced from the DNA sequence, that has 2 different amino acids. The nucleotide and deduced amino acid sequences are shown in SEQ ID NOS. 30 and 31, respectively.

Plasmid pMYC1636 was introduced into an acrystalliferous (cry−) B.t. host by electroporation. Expression of an approximately 68 kD processed protein was verified by SDS-PAGE.

EXAMPLE 12
Insertion of Toxin Genes Into Plants

One aspect of the subject invention is the transformation of plants with genes encoding a calliphorid toxin. The transformed plants are resistant to attack by calliphorids.

Genes encoding calliphorid-active toxins, as disclosed herein, can be inserted into plant cells using a variety of techniques which are well known in the art. For example, a large number of cloning vectors comprising a replication system in E. coli and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into E. coli. The E. coli cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 13

Cloning of Novel *B.t.* Genes Into Insect Viruses

A number of viruses are known to infect insects. These viruses include, for example, baculoviruses and entomopoxviruses. In one embodiment of the subject invention, calliphorid-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

EXAMPLE 14

Activity Against Blowfly Pests

A technical powder containing 30% biomass was prepared. The powder was mixed with newborn calf serum to a concentration of 50,000 ppm. Dental plugs were saturated with the solution. Newly hatched sheep blowfly maggots were exposed to the saturated plugs. Maggot mortality was assessed 24 and 48 hours after initial exposure.

TABLE 4

| B. t. Strain | Percent Mortality |
| --- | --- |
| PS123D1 | 98.5 |
| PS71M3 | 99.5 |
| PS63B2 | 95.0 |
| PS52A1 | 98.5 |
| PS80JJ1 | 99.5 |
| PS204G6 | 97.5 |
| PS91C2 | 80.0 |
| PS173A | 100.0 |
| PS31J2 | 87.5 |
| PS201T6 | 100.0 |
| PS86Q3 | 97.5 |
| PS74G1 | 100.0 |
| PS33F2 | 95.0 |
| PS202U2 | 90.0 |
| PS83E5 | 99.5 |
| PS84C3 | 95.0 |
| PS204C3 | 80.0 |
| PS207B6 | 90.0 |
| PS211B2 | 94.0 |
| Control | 4.0 |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling pests of the family Calliphoridae, which comprises contacting said pests with a calliphorid-controlling amount of a *Bacillus thuringiensis* (*B.t.*) microbe *B.t.* PS204C3 or a toxin from said microbe.

2. The method, according to claim 1, wherein said pest is selected from the group consisting of blowflies and screwworms.

3. The method, according to claim 1, which further comprises administration of one or more additional calliphorid-controlling compounds.

4. The method, according to claim 1, wherein said toxin is administered as a drench.

5. The method, according to claim 1, wherein said toxin is administered in a bait bin.

6. A composition of matter for controlling pests of the family Calliphoridae comprising a *Bacillus thuringiensis*

(*B.t.*) microbe *B.t.* PS204C3 or a toxin from said microbe, in association with a carrier particularly suited for use in treating calliphorids.

7. The composition, according to claim 6, which further comprises one or more additional calliphorid-controlling compounds.

8. A biologically pure culture of *Bacillus thuringiensis* PS204C3.

* * * * *